United States Patent [19]
Dahlgren

[11] 3,976,594
[45] Aug. 24, 1976

[54] PRESERVATIVE FOR WOOD AND OTHER ORGANIC MATERIAL SUBJECT TO BIOLOGICAL DETERIORATION AND CONTAINING AMINE-FORMING METALS, POLYPHOSPHATE AND CHLORINATING PHENOLS

[75] Inventor: Sven-Eric Dahlgren, Landskrona, Sweden

[73] Assignee: Boliden Aktiebolag, Stockholm, Sweden

[22] Filed: Apr. 15, 1974

[21] Appl. No.: 460,902

[30] Foreign Application Priority Data
Apr. 27, 1973 Sweden .............................. 7305979

[52] U.S. Cl. ..................... 252/400 A; 252/400 R; 252/401; 252/404; 21/7
[51] Int. Cl.² ................. C09K 15/32; C09K 15/16; C09K 15/08; B27K 3/00
[58] Field of Search ............ 252/400 A, 400 R, 401, 252/404, 407; 21/7, 58

[56] References Cited
UNITED STATES PATENTS

| 959,505 | 5/1910 | Gerlache | 21/7 |
| 1,082,658 | 12/1913 | Somermeier | 21/7 |
| 2,637,661 | 5/1953 | Benignus | 21/58 |
| 2,908,542 | 10/1959 | Farber | 21/7 |
| 3,284,157 | 11/1966 | Peters | 21/7 |
| 3,464,782 | 9/1969 | Ricard | 21/7 |
| 3,657,412 | 4/1972 | Reuther | 21/7 |
| 3,702,784 | 11/1972 | Farquhar | 21/58 |

FOREIGN PATENTS OR APPLICATIONS

| 845,024 | 6/1970 | Canada |
| 182,477 | 2/1963 | Sweden |
| 202,417 | 3/1966 | Sweden |
| 11,286 | 8/1900 | Sweden |

Primary Examiner—Samuel W. Engle
Assistant Examiner—Donald P. Walsh
Attorney, Agent, or Firm—Stevens, Davis, Miller & Mosher

[57] ABSTRACT

A preservative for wood and other organic materials subject to biological deterioration. The preservative contains an amine-forming biologically active metal; polyphosphate, amine, chlorinated phenols and carbon dioxide. The mole ratios between polyphosphate and amine-forming metal is 0.5 – 1.5, between amine and amine-forming metal 1 – 7; between amine and carbon dioxide 1 – 4 and between amine-forming metal and chlorinated phenole, calculated as pentachlorophenol 0.5 – 15.

10 Claims, 1 Drawing Figure

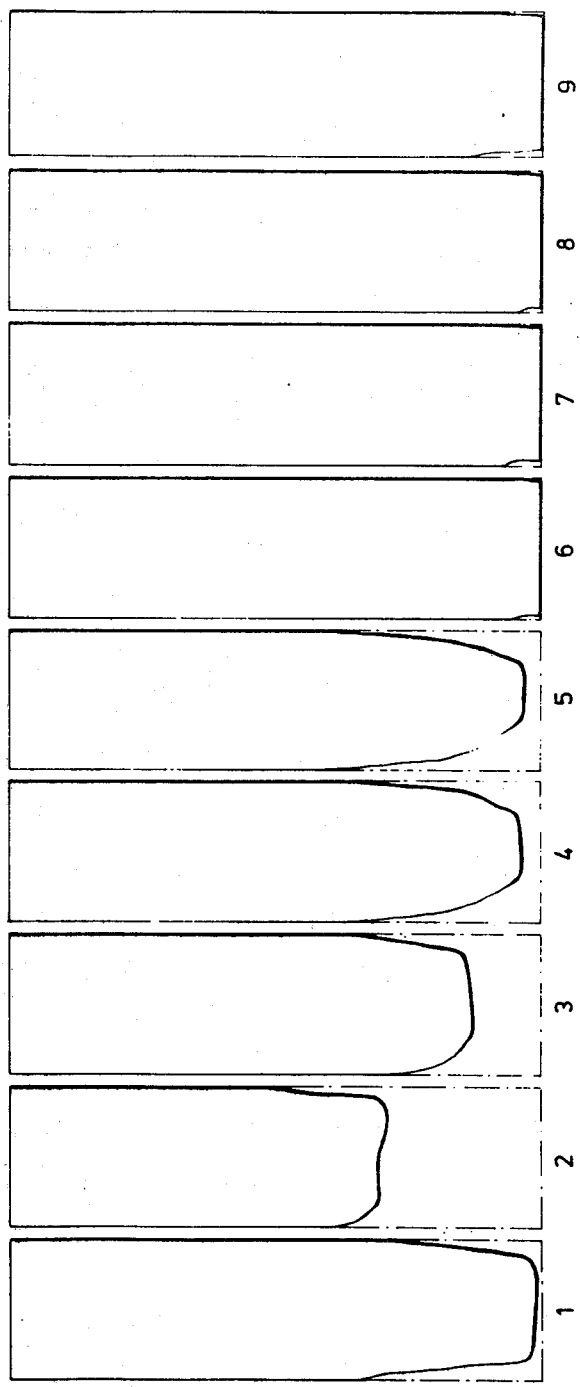

PRESERVATIVE FOR WOOD AND OTHER ORGANIC MATERIAL SUBJECT TO BIOLOGICAL DETERIORATION AND CONTAINING AMINE-FORMING METALS, POLYPHOSPHATE AND CHLORINATING PHENOLS

The present invention relates to a water-soluble preservative for wood and other organic materials subjected to biological deterioration.

The preservative according to the invention contains amine-forming metals which are active against biological attack, polyphosphates and amines both in balanced proportions which are intended to maintain the metal in solution by sequestration, carbon dioxide for regulating the pH of the solution of the preservative, and chlorinated phenols for complementing the biological activity spectrum of said agent. In accordance with the invention, the preservative may also be given certain fire-retardant properties.

Impregnating agents which contain amine-forming metals and chlorinated phenols are previously known, e.g., from Swedish Pat. Nos. 182,404, 182,477 and 202,417, according to which the metal is dissolved in an aqueous solution containing ammonia and carbon dioxide. Other preservatives containing amine-forming metals together with arsenic or also ortho-phosphate are known, e.g., from U.S. Pat. No. 2,149,284, Canadian Pat. No. 845,024 and Swedish patent application 6439/1972.

If the composition of a preservative is such that when the agent is fixed there is formed basic copper carbonates or similar compounds which are decomposited at moderately increased temperatures, an extremely active metal oxide (copper oxide) is formed when the fixed compound is heated. This active metal oxide has an extremely high catalytic effect on combustion processes especially with respect to so called after-glow. By after-glow is meant here and in the following a combustion process without visible flames. Consequently, an impregnating agent with which fixing of the agent is obtained by the formation of basic copper carbonates or similar compounds is not suitable for use with building timber, unless the preservative contains an additive which inhibits said so-called after-glow processes.

The preservative according to the invention is mainly characterized in that said agent contains an amine-forming biologically active metal selected from the group copper, zinc, cobalt and nickel, polyphosphate, amine, chlorinated phenols and carbon dioxide, and in that the mole ratio of polyphosphate:amine-forming metal is 0.5 – 1.5, the mole ratio of amine:amine-forming metal is 1 – 7, the mole ratio of amine: carbon dioxide is 1 – 4 and the mole ratio of amine-forming metal:chlorinated phenols calculated as pentachlorophenol is 0.5 – 15.

The amine-forming metal may be copper and/or zinc, and the amine may be ammonia.

According to one feature of the invention at least half the amine incorporated in the impregnating agent is ammonia while the remainder is an organic amine, such as mono ethanolamine for example.

Thus, the invention is mainly characterized in that the major portion of the amine-forming metal is complex bound with polyphosphate, thereby affording the advantage whereby the aforementioned combustion processes are counteracted. In this way there is obtained an preservative with which amine-forming metal in combination with chlorinated phenols is able to protect against the aforementioned after-glow processes. As before mentioned, this has not previously been possible. By chlorinated phenols is meant primarily pentachlorophenol although tetrachlorophenol, trichlorophenol and other chlorinated phenols may be used. The technical product contains a mixture of different chlorinated phenols, and is normally chlorinated to approximately 88 – 90% to pentechlorophenol. Further chlorination results in the formation of secondary products having split benzene rings. Different polyphosphates have different complex forming ability and are also dependent on pH, with a maximum on the alkaline side. By polyphosphate is meant diphosphate, triphosphate and tetraphosphate, although in accordance with the invention diphosphate or triphosphate are primarily used. The best results have been obtained with diphosphate. The diphosphate may contain at most two equivalents of alkali metals. The term "polyphosphate" also includes metaphosphates. A satisfactory complex formation cannot be obtained solely with polyphosphate, but that in order for the solution to obtain suitable solubilizing properties and stability it is necessary to include a supplementary complex forming agent. Such properties are obtained by supplementing the solution with an amine, which may be ammonia and/or an organic amine. Examples of organic amines are hydroxyalkyl amines such as monoethanol amine, diethanol amine, triethanol amine and aminoacetic acid. Different types of complexes occur simultaneously with the amino-forming metal, these being:

anionic complexes with polyphosphate
anionic double complexes with polyphosphate and amine, and
cationic complexes with amine.

The requisite quantity of amine can be reduced in comparison with the impregnating agents described in the aforementioned patents by using polyphosphate as a complex forming agents. This means that the ammonia vapour pressure over the impregnating agent solution is, at the same time, greatly lowered in comparison with preparations which do not contain polyphosphate, which result in a far less pronounced smell of ammonia when carrying out the impregnating process. The concentration of free ions of the amine-forming metal, the preservative solution, i.e. ions which are not complex bound, must be so low that the metal does not cause chlorinated phenols to precipitate, said phenols being calculated here as pentechlorophenol. Ammonium pentachlorophenolate is only slightly soluble, but the formation of this compound is strongly inhibited. To counteract the formation of ammonium pentachlorophenolate in the impregnating solution used, the pH of the solution should not be excessively high. Further, the pH value upon contact of the impregnating solution with the wood substance to be impregnated should be sufficiently high to prevent the precipitation of pentechlorophenol, since such precipitation would prevent complete penetration of the impregnating solution into the wood. If such precipitation takes place during the impregnating process, the conveying passages in the wood become blocked to a greater or lesser extent.

Wood substances have a certain ion exchange capacity, which makes it necessary to compensate the composition of the preservatives with respect to the ions preferentially taken up by said substances. An impregnating agent comprising copper sulphate, tetrasodium diphosphate, ammonia or monoethanol amine and sodium pentachlorophenolate provides a solution with a pH of 9 – 10 and a pH upon contact with a wood substance (pine-wood) of approximately 5. This means that the pH is too low to prevent the precipitation of pentachlorophenolate. The pH can be controlled by adding carbon dioxide to the amine incorporated in the preservative. The pH of an impregnating solution can be balanced to a pH of beneath 8.5, so that the decrease in pH upon contact with said wood substance is limited to some tenths of a pH unit. Thus, in this latter instance precipitation will not take place during the actual impregnating process. The preservative is fixed by the decrease in pH which takes place as the preservative dries, whereupon the ammonia evaporates. This decrease in pH also causes the sequestering ability of the diphosphate to greatly decrease or to become nonexistent, and the solubility of chlorinated phenols to decrease to the vicinity of zero, irrespective of the form in which the precipitation of said phenols take place.

In order to obtain protection against the aforementioned after-glow processes with phosphates, i.e. processes with which there is no visible flame, it would appear that phosphoric acids must be released at elevated temperatures. This does not take place when using neutral alkali polyphosphates, such as tetrasodium diphosphate or pentasodium triphosphate, although such phosphates are satisfactory with respect to the remaining, desired properties of the preservative. Defined ammonium polyphosphates are not commercially available. It is possible, however, to use, e.g. disodium dihydrogen diphosphate and to compensate with amines, to obtain full neutralization. Preservatives prepared while observing this latter consideration have been found to give good protection against fire. This has been proven with tests made with the impregnating agent according to the invention and a commercially available preservative. The invention is illustrated in the following examples, shown in table 1 below. The table shows a number of different compositions for preservative prepared according to the invention. The table also shows for respective examples the mole ratios between pyrophosphate and metal, between ammonia and metal, between amine (ethanol amines : HM) and metal, and between the total quantity of ammonia together with amine and carbon dioxide. Additionally, the table also shows the mole ratio between metal and pentachlorophenol (PCP), and the concentration and the pH of the solution. Table 2 shows the results of tests carried out on the after-glow of pine sapwood rods, which had been Lowry-impregnated with a commercially available preparation according to Swedish Pat. Nos. 182,404, 182,477 and 202,417 and with different preservatives according to the invention, the composition of which latter agents is shown in Table 1. As mentioned, the tests were carried out on pine sapwood rods which had been dried at room temperature and which had a size of 28 mm × 28 mm × 100 mm. The rods were impregnated by the so-called Lowry-impregnation method and were dried to the same weight possessed by said rods prior to said rods being impregnated. The Lowry-impregnation method is effected by exposing dry wood to an impregnating liquid and then subjecting the wood to pressure. The wood is dried after being impregnated.

Subsequent to impregnating the rods, the rods were dried and placed in a chamber free from draft conditions. The rods were suspended with their lower end at a distance of 100 mm above a Meker-burner, which operated on town-gas and which had a diameter of 25 mm. 250 liters of gas were charged to the burner each hour and the burner operated with a fully open air intake.

The test rods were ignited under exactly 30 seconds and were permitted to burn under draft-free conditions until they extinguished. The major portion of the combustion process took place without visable flame, i.e. so-called after-glow.

Upon completion of the combustion process, ash was brushed from the rods with a soft brush and the sample rods were weighed. Five rods were used in each test and the weight losses recited in table 2 constitute an average value for said five samples. The standard deviation between the samples is given in the table. The tests were carried out with a composition corresponding to the normal concentration recommended for similar preservative and with half of this concentration. The obtained results show the retention of impregnating solution, the loss in weight upon combustion of the samples and the standard deviations for the obtained values on weight loss. In order for the tests to be assessed satisfactorily, the appearance of the sample rods subsequent to the test should also be observed, in addition to the loss in weight. The FIGURE therefore also shows the configuration of the sample rods subsequent to the test. In the FIGURE shows 1. A reference sample
2. Test according to Swedish Pat. No. 182,404 with 0.30% Cu
3. Test according to Swedish Pat. No. 182,404 with 0.15% Cu
4. Test according to the present invention, Example 1 0.20% Cu
5. Test according to the present invention, Example 3 0.30% Cu
6. Test according to the present invention, Example 6 0.20% Cu
7. Test according to the present invention, Example 6 0.10% Cu
8. Test according to the present invention, Example 7 0.30% Cu
9 Test according to the present invention, Example 7 0.15% Cu The reference sample, which comprised untreated wood, shows a modest change of configuration, despite the fact that the loss in weight is close to 30%, which indicates a high degree of charring. The commercially available products according to Swedish Pat. Nos. 182,404, 182,477 and 202,417 show a great change in configuration, despite the fact that the loss in weight has increased by the order of magnitude of only 10%. This indicates that the sample rods had a quite considerable after-glow. With the agent according to the examples 1 and 2, the loss in weight is the same as that for the reference sample, although the change in configuration is greater. This indicates a certain but limited afterglow. With the impregnating agent according to examples 6 and 7, the loss in weight is greatly reduced and the change in configuration is negligable. In this latter case the aforementioned afterglow processes have been substantially eliminated.

Table 1

Examples of compositions of impregnating agent

| Mole ratios | | Ex. 1 | Ex. 2 | Ex. 3 | Ex. 4 | Ex. 5 | Ex. 6 | Ex. 7 |
|---|---|---|---|---|---|---|---|---|
| $Na_4P_2O_7/CuSO_4$ | | 1 | 1 | 1 | — | — | — | — |
| $Na_4P_2O_7/ZnSO_4$ | | — | — | — | 1 | — | — | — |
| $Na_2H_2P_2O_7/CuSO_4$ | | — | — | — | — | — | 1 | 1 |
| $Na_5P_3O_{10}/CuSO_4$ | | — | — | — | — | 1 | — | — |
| $NH_3/Cu(Zn)$ | | 4 | 2 | 4 | 5 | 4 | 6 | 6 |
| HM/Cu | | — | 2 | — | — | — | — | — |
| $(NH_3+HM)/CO_2$ | | 2 | 2 | 2 | 2 | 2 | 3 | 3 |
| Cu(Zn)/PCP | | 3,34 | 3,34 | 8,35 | 3,37 | 3,34 | 3,34 | 8,35 |
| Concentration | % Cu | 0.20 | 0.20 | 0.30 | — | 0.20 | 0.20 | 0.30 |
| in | % Zn | — | — | — | 0.21 | — | — | — |
| solution | % PCP | 0.25 | 0.25 | 0.15 | 0.25 | 0.25 | 0.25 | 0.15 |
| pH at | in solution | 8.15 | 8.50 | 8.15 | 8.50 | 8.15 | 7.85 | 7.80 |
| 20°C | solution + pine sapwood* | 7.80 | 7.70 | 7.95 | 7.80 | 7.30 | 7.55 | 7.70 |

| Mole ratios | | Ex 8 | Ex 9 |
|---|---|---|---|
| $Na_2H_2P_2O_7/CoSO_4$ | | 1 | — |
| $Na_2H_2P_2O_7/NiSO_4$ | | — | 1 |
| $NH_3/Co(Ni)$ | | 7 | 7 |
| $NH_3/CO_2$ | | 2 | 2 |
| Co(Ni)/PCP | | 3,34 | 3,34 |
| Concentration | % Co | 0.19 | — |
| in | % Ni | — | 0.19 |
| solution | % PCP | 0.25 | 0.25 |
| pH at | in solution | 8.15 | 7.60 |
| 20°C | in solution + sapwood | 7.30 | 7.10 |

HM = monoethanolamine.
PCP = chlorinated phenols calculated as $C_6CL_5O^-$. Added as sodium salt.
*6 g of air-dry pine sapwood sawdust + 8 ml solution

TABLE 2

Tests carried out on the after-glow of pine sapwood rods Lowry-impregnat with different types of impregnating agents containing copper and chlorinated phenols. Impregnating pressure 1.1 MPa. Moisture ratio approximately 10%*.

| Agent | Copper content in the solution in percent | Retention of impregnating solution in g per 100 g wood, average value for five sample rods | After-glow Weight loss in percent. Average value for five sample rods | The standard deviation of the loss in weight |
|---|---|---|---|---|
| Reference sample, untreated wood | — | — | 27 | 2 |
| Acc. to Swedish pat. app. 182 404 182 477 and 202 417 Commercially available product | 0.30 | 92 | 40 | 5 |
| | 0.15 | 94 | 34 | 4 |
| Acc. to Ex. 1 | 0.20 | 84 | 28 | 3 |
| | 0.10 | 91 | 24 | 3 |
| Acc. to Ex. 2 | 0.30 | 92 | 28 | 2 |
| | 0.15 | 89 | 27 | 2 |
| Acc. to Ex. 6 | 0.20 | 99 | 8 | 1 |
| | 0.10 | 104 | 10 | 2 |
| Acc. to Ex. 7 | 0.30 | 87 | 6 | 1 |
| | 0.15 | 93 | 8 | 1 |

*moisture ratio is equal to moisture/dry weight

I claim:

1. A water-soluble preservative for wood and other organic materials subject to biological deterioration, containing an amine-forming biologically active metal selected from the group consisting of copper, zinc, cobolt, nickel and mixtures thereof; polyphosphate; amine; chlorinated phenols and carbon dioxide, and in that the mole ratio of polyphosphate:amine-forming metal is 0.5 – 1.5, the mole ratio of amine:amine-forming metal is 1 – 7, the mole ratio of amine:carbon dioxide is 1 – 4 and the mole ratio of amine-forming metal:chlorinated phenols calculated as pentachlorophenol is 0.5 – 15.

2. A preservative according to claim 1, wherein the amine-forming metal is copper and/or zinc.

3. A preservative according to claim 1, characterized in that the amine is ammonia.

4. A preservative according to claim 1, characterized in that at least half of the amount of the amine is ammonia and the remainder is an organic amine.

5. A preservative according to claim 4, characterized in that the organic amine is monoethanolamine.

6. A preservative according to claim 1, characterized in that the polyphosphate is diphosphate.

7. A preservative according to claim 1 and 6, characterized in that the diphosphate contains at most two equivalent alkali metals.

8. A preservative according to claim 1, characterized in that the polyphosphate is triphosphate.

9. A preservative according to claim 1, characterized in that the poyphosphate is ammonium polyphosphate.

10. A preservative according to claim 1, characterized in that the chlorinated phenol is a commercial grade of pentachlorophenol.

* * * * *